US006516216B1

(12) United States Patent
Fontenot et al.

(10) Patent No.: US 6,516,216 B1
(45) Date of Patent: *Feb. 4, 2003

(54) CIRCUMFERENTIAL TRANSILLUMINATION OF ANATOMIC JUNCTIONS USING LIGHT ENERGY

(75) Inventors: Mark G. Fontenot, Lafayette, LA (US); Richard Feinberg, Bellingham, WA (US); Jim Vining, Yuma, AZ (US)

(73) Assignee: Stryker Corporation, Kalamazoo, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/606,106

(22) Filed: Feb. 23, 1996

(51) Int. Cl.[7] ................................................. A61B 5/00
(52) U.S. Cl. ....................................... 600/473; 600/476
(58) Field of Search ................................ 128/664, 665, 128/653.1, 899, 634; 600/109, 160, 178; 606/7, 8, 15, 16

(56) References Cited

U.S. PATENT DOCUMENTS

| | | | |
|---|---|---|---|
| 3,674,008 A | * | 7/1972 | Johnson |
| 3,886,933 A | | 6/1975 | Mori |
| 4,248,214 A | * | 2/1981 | Hannah et al. |
| 4,751,571 A | | 6/1988 | Lillequist |
| 4,806,761 A | | 2/1989 | Carson et al. |
| 4,898,175 A | | 2/1990 | Noguchi |
| 5,066,292 A | * | 11/1991 | Muller et al. ................. 606/7 |
| 5,168,873 A | | 12/1992 | Seifert et al. |
| 5,187,572 A | | 2/1993 | Nakamura |
| 5,394,863 A | * | 3/1995 | Sanford et al. |
| 5,423,321 A | | 6/1995 | Fontenot |
| 5,449,354 A | * | 9/1995 | Konwitz et al. ............... 606/15 |
| 5,451,221 A | * | 9/1995 | Cho et al. ........................ 606/3 |
| 5,517,997 A | * | 5/1996 | Fontenot ....................... 128/664 |

FOREIGN PATENT DOCUMENTS

| | | |
|---|---|---|
| GB | 2102127 | 3/1985 |
| WO | WO/91/11956 | 8/1991 |

OTHER PUBLICATIONS

"Laparoscopic Transillumination—for the Location of Anterior Abdominal Wall Blood Vessels", Elisabeth H. Quint, M.D., et al, Journal of Laparoendoscopic Surgery, vol. 6, No. 3, 1996; pp. 167–169.
"An Investigation of an Infrared Ray Electronic Endoscope with a Laser Diode Light Source", H. Kohso et al, Endoscopy 22 (1990) pp. 217–220.
"Light Reflection Rheography: A Saimple Noninvasive Screening Test for Deep Vein Thrombosis", Subodh Arora et al, Journal of Vascular Surgery, Nov. 1993, pp. 767–772.
"Indocyanine Green Dye Fluorescence and Infrared Absorption Choroidal Angiography Performed Simultaneously with Fluorescein Angiography", R.W. Flower and B.F. Hochheimer, The Johns Hopkins Medical Journal, vol. 138 No. 2, Feb. 1976, pp. 33–37.

* cited by examiner

Primary Examiner—Marvin M. Lateef
Assistant Examiner—Shawna J Shaw
(74) Attorney, Agent, or Firm—Flynn, Theil, Boutell & Tanis, P.C.

(57) ABSTRACT

Apparatus is provided that provides a ring of light around a junction to be viewed; the ring of light being bright enough to be seen on the other side of the junction. Such an arrangement may be used in severing an anatomic body, such as the cervix, from the vagina whereby a surgeon viewing the structure from the pelvic cavity has the junction outlined in light brought into contact with the junction through the vagina.

22 Claims, 10 Drawing Sheets

CIRCUMFERENTIAL TRANSILLUMINATION OF ANATOMIC JUNCTIONS USING LIGHT ENERGY

FIELD OF THE INVENTION

The present invention relates to methods and apparatus for circumferential transillumination of junctions between anatomic structures of a living body to allow surgeons to identify these junctions and guide incisions during surgical procedures and more specifically assisting in locating and/or avoiding such junctions.

BACKGROUND OF THE INVENTION

Separating the cervix from the vagina during surgical procedures may be difficult. McCartney and Johnson (1995) reported on the use of a vaginal tube to separate the uterus from the vagina during laparoscopic hysterectomy which overcomes this difficulty by placing a wide bore plastic tube in the vagina to expose the cervico-vaginal junction and stretch the vaginal fornices. The stretched vagina falls away from the cervix as the surgeon attempts to locate the most distal aspect of the tube as it protrudes into the pelvic cavity. Palpation using an instrument during laparoscopy is frequently used to discover the distal aspect of the tube at which time the surgeon employs diathermy or other means to cut tissue overlying the tube. The protruding tube in the pelvic cavity presents a ridge which requires the surgeon to continually palpate the distal aspect of the tube in order to locate the cervico-vaginal junction and eventually to facilitate proper guidance of the incision. The procedure is difficult, time consuming and at times leads to problems.

OBJECTS OF THE INVENTION

It is an object of the present invention to provide a device which circumferentially transilluminates a junction between anatomic structures using visible light or infrared light or combination of visible and infrared light so as to precisely locate such junction and warn the surgeon of imminent approach thereto.

It is another object of the present invention to provide a method of precisely locating junctions or valves and the like whereby a surgeon can easily visualize and can either invade or avoid the transilluminated junction or valve.

BRIEF DESCRIPTION OF THE PRESENT INVENTION

The present invention overcomes and eliminates the need for the surgeon to palpate the distal aspect of a vaginal tube by using light energy to circumferentially transilluminate the cervico-vaginal junction. Furthermore, the invention can employ the same emission-detection technology described in U.S. Pat. No. 5,423,321 entitled "Electronic Detection of Anatomic Passages Using An Infrared Emitting Catheter." The patent provides for transillumination of passages using an infrared emitting catheter. In one embodiment described in the patent, ureteral identification is intended to assist the surgeon with the management of the ureters during laparoscopic and open surgical procedures. When coupled to an infrared illuminator and placed in the ureter, an emitting fiber emits infrared light. Infrared transillumination of the ureter is not visible to the human eye. Thus electronic detection of the transilluminated ureter is facilitated using either a video system that employs an infrared sensitive imaging system or audible system which emits an audible tone when an infrared sensitive detector probe senses infrared light.

The differences between the aforementioned art and the invention centers on circumferential transillumination of a junction compared to transillumination of a passage and the use of visible light with or without an infrared component. For example, the invention may employ the same emitting fiber described in the patent. The emitting segment of the emitting fiber is circumferentially bonded to the distal aspect of a cup or tube seated substantially in contact with the cervico-vaginal junction, thus resulting in the circumferential junctional transilluminator of the invention. Therefore, transferring light energy to the emitting fiber and the emitting segment at the distal aspect of the circumferential junctional transilluminator permits detection of the transilluminated junction using the same method and devices described in the patent. Visible light, however, may also be used as another energy band to transilluminate the junction, in which case the eye or a typical medical endoscopic camera, or a camera could be used to detect the junction.

No prior materials known to the applicants disclose the concept of employing visible or infrared light or a combination of both to circumferentially transilluminate junctions between living structures such as the cervico-vaginal junction.

The present invention is described as employed to precisely locate the cervico-vaginal junction to reduce the danger to this junction particularly during performance of a hysterectomy. The present invention, referred to as the CJT, and associated detection system of the present invention is not limited to such use, but this use is illustrative of the utility of the apparatus and method.

Light energy with or without a component of infrared light energy or infrared light energy with or without a component of visible light energy can be used to transilluminate the cervico-vaginal junction using the CJT. The infrared emission-detection technology of the '321 patent is currently in commercial use as the INFRAVISION Illuminator System with an application for ureteral identification and is readily applicable to the present invention. When the light energy emitter is coupled to the INFRAVISION IR Illuminator and placed in the ureter, the emitting fiber emits infrared light. Infrared transillumination of the ureter is not visible to the human eye. Detection of the transilluminated ureter is facilitated using either the INFRAVISION Imaging System or the INFRAVISION Detector Probe.

To combine the present invention with the art described in the patent requires the CJT to be coupled to the INFRAVISION IR Illuminator to provide modulated infrared light energy to transilluminate the cervico-vaginal junction. Since the human eye is not sensitive to infrared light energy, the INFRAVISION Imaging System and/or the INFRAVISION Detector Probe is used to locate the cervico-vaginal junction.

The INFRAVISION IR Illuminator consists of two electronic modules, a laser light source and light sensor housed in one unit. The INFRAVISION IR Illuminator is DC powered through an AC/DC power supply; is non-sterile; and reusable. The INFRAVISION IR Illuminator houses two variable 250 mW infrared laser diodes (laser light source); and has a photodetector and circuitry that is tuned to the modulation frequency and wavelength of the laser diodes (light sensor). The emitting fiber residing at the most distal aspect of the CJT is coupled to the INFRAVISION IR Illuminator which provides infrared light energy to transilluminate the junction. The INFRAVISION Imaging System consists of an infrared sensitive camera and camera control unit. The INFRAVISION Imaging System is sensitive to visible and infrared light, and is intended to detect the specific wavelength of the infrared transilluminated cervico-vaginal junction and display an image of the junction on a video monitor.

The CJT for the cervico-vaginal junction takes the form of a hollow cone with a narrow light emitting surface or edge at the base of the most distal aspect of the cone. The hollow cone is made preferably from plastic. Attached to the apex of the cone is a handle that facilitates introduction of the cone into the vaginal canal and which is used to press the base of the cone against the cervico-vaginal junction. The emitting fiber is housed in the handle and emerges at the apex of the cone and is secured to the edge of the base or most distal aspect of the cone. The light emitting segment diffuses light radially. The proximal end of the emitting fiber has an optical connector that couples to the infrared laser diodes of the INFPAVISION IR Illuminator. When the CJT is coupled to the INFRAVISION IR Illuminator and its distal end/aspect is placed against the cervico-vaginal junction, the CJT transilluminates the pelvic cavity.

For circumferential infrared transillumination of the cervico-vaginal junction, the CJT employed with the INFRAVISION Illumination System is used as follows. After the vaginal area is prepared for surgery, the distal aspect of the CJT is introduced into the vaginal canal and placed over the cervix and against the cervico-vaginal junction. The emitting fiber is connected to the INFRAVI-SION IR Illuminator which launches infrared light energy into the emitting fiber. The cervico-vaginal junction is transilluminated since the emitting segment of the emitting fiber, which is bonded to the edge of the cone, allows light to diffuse radially and traverse into the abdomino-pelvic cavity. During laparoscopic procedures, the INFRAVISION Imaging System detects and projects the infrared transillu-minated cervico-vaginal junction onto the video monitor. During difficult surgical cases when the cervico-vaginal junction is embedded in dense fibrous tissue, the detector probe can be introduced into the pelvic area through a trocar. Visualization of the detector probe tip on the video monitor allows the surgeon to position and maneuver the detector probe in the approximate area of the infrared transillumi-nated cervico-vaginal junction. The detector probe is positioned and maneuvered until an audible sound is broadcast from the Light Sensor panel of the INFRAVISION IR Illuminator, which indicates detection of the infrared tran-silluminated cervico-vaginal junction. During open surgical procedures, the detector probe is introduced into the abdo-men and pelvic areas and positioned in the approximate area of the cervico-vaginal junction. The detector probe is maneuvered until an audible sound is broadcast from the INFRAVISION IR Illuminator, which indicates detection of the infrared transilluminated cervico-vaginal junction.

The above and other features, objects and advantages of the present invention, together with the best means contem-plated by the inventor thereof for carrying out the invention will become more apparent from reading the following description of a preferred embodiment and perusing the associated drawings in which:

DETAILED DESCRIPTION OF THE PRESENT INVENTION

Figure 2:
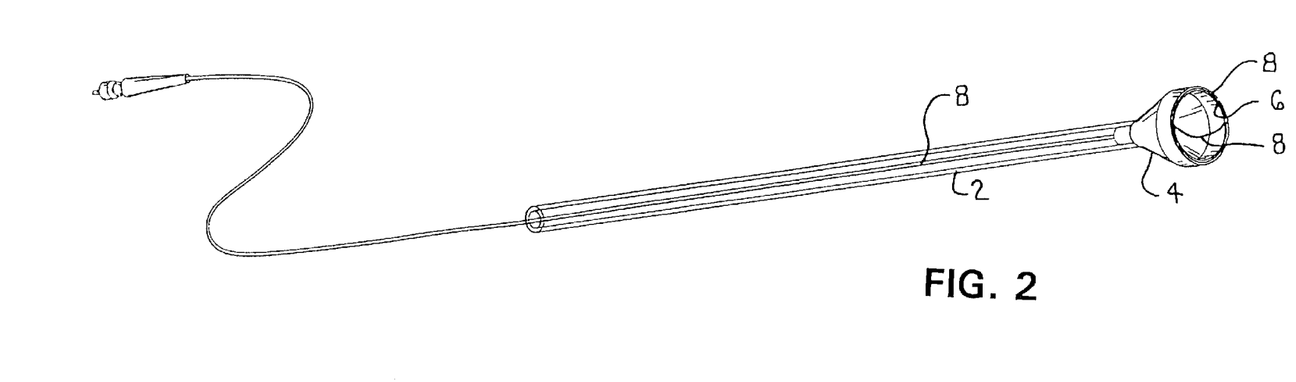
FIG. 2 is an isometric view of the CJT using an emitting fiber with the emitting segment bonded circumferentially to the distal edge of a cone.
Figure 3:
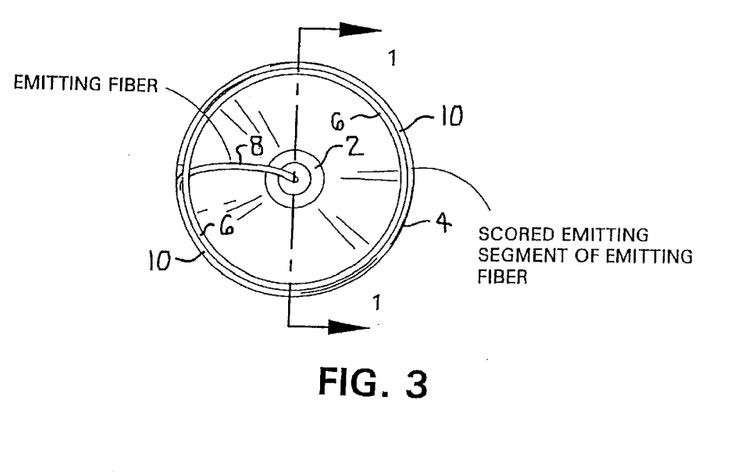
FIG. 3 is an end view of the distal edge of a cone showing the emitting fiber emerging from the handle and the emitting segment bonded to the edge.
Figure 4:
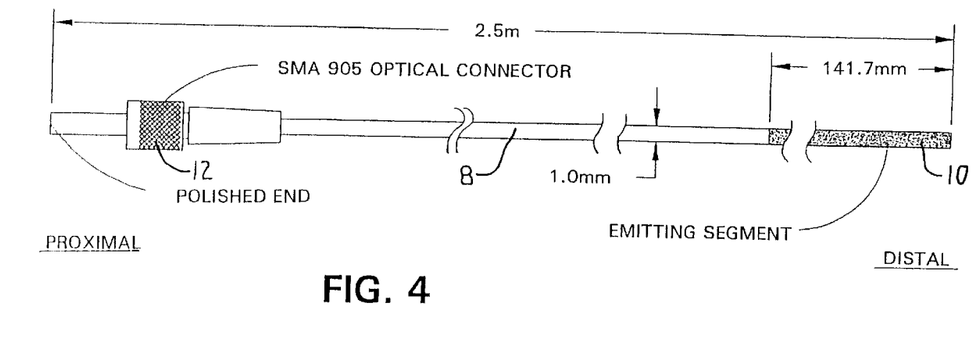
FIG. 4 shows a side view of the emitting fiber with the emitting segment used in the fabrication of the CJT.

Referring to FIGS. 1, 2, 3 and 4 of the accompanying drawings, the CJT in accordance with the invention com-prises a handle 2 attached to the virtual apex of a hollow cone 4. The distal aspect of the cone has an edge 6 to receive an emitting fiber 8. The distal portion of the emitting fiber (ESKA SK-40) is scored at 10 to form the emitting segment as shown in FIG. 4. The region 10 of the fiber is circum-ferentially bonded to the edge 6 of the cone 4 using epoxy or the like. The emitting fiber has an optical connector 12 (SMA-905) fitted at its proximal end. The emitting fiber is secured to the inside wall 14 of the cone 4 as it passes out of the handle. The emitting segment bonded to the edge of the cone allows light to exit the wall of the end of the emitting fiber 8 resulting in a circumferential light emitting junctional transilluminator.

Figure 1:
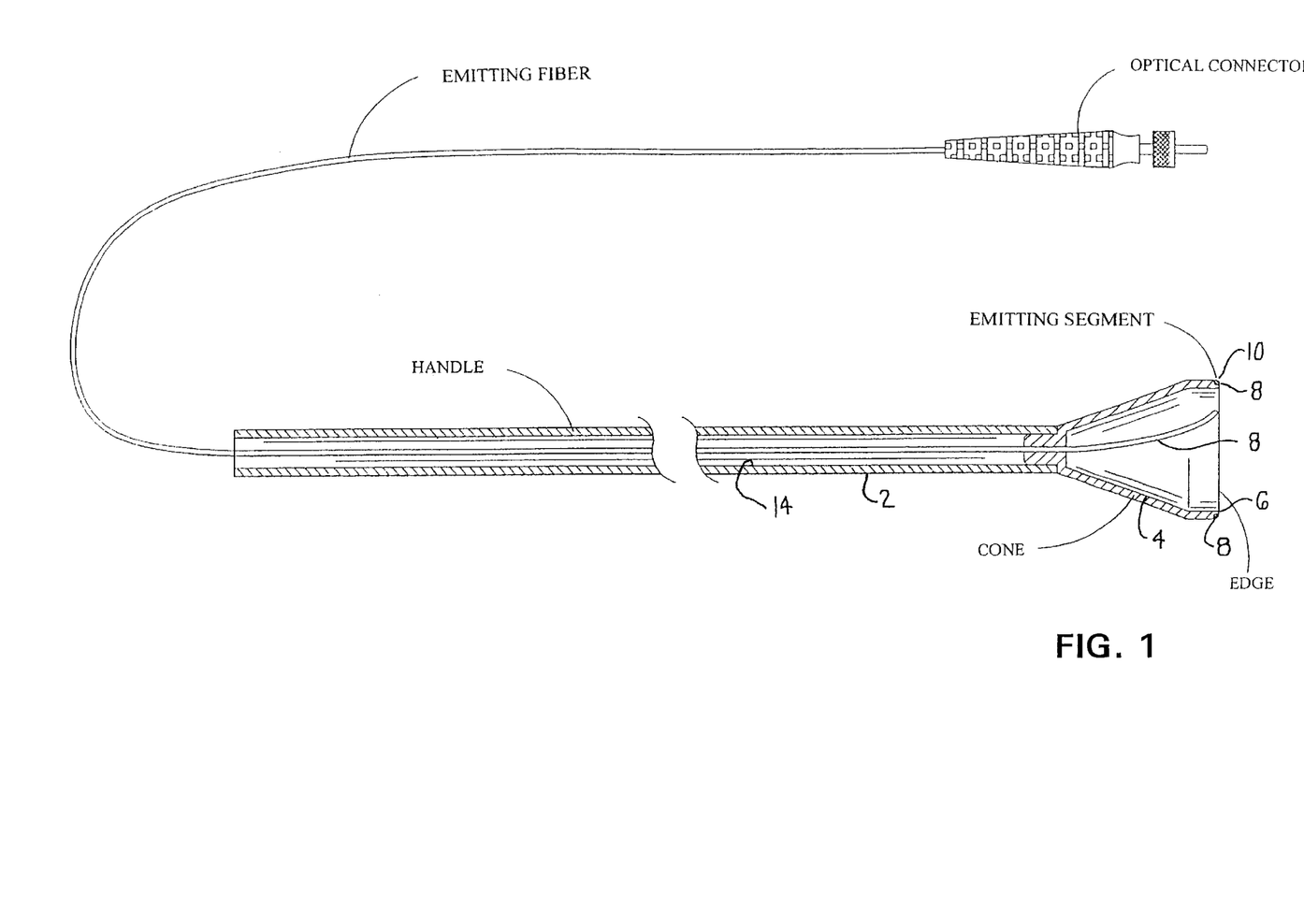
FIG. 1 is a longitudinal view of the CJT using an emitting fiber with the emitting segment bonded circumferentially to the distal edge of a cone.

The emitting segment can be selectively abraded or scored so as to allow light to be emitted such that the entire cervico-vaginal junction (circumferential transillumination) or only a portion of the junction (semicircumferential) is transilluminated. The outer diameter of the cone 4 in a typical rendition of the invention shown in FIGS. 1, 2 and 4 is 45 mm with an edge thickness of 1 mm. The length of the emitting segment circumferentially bonded to the edge is approximately 141.4 mm and the radius of the distal end of the cone 4 is approximately 22.5 mm. The length of the handle shown in FIGS. 2 and 3 is 45 cm and the length of the emitting fiber is 2.5 m.

Figure 5:
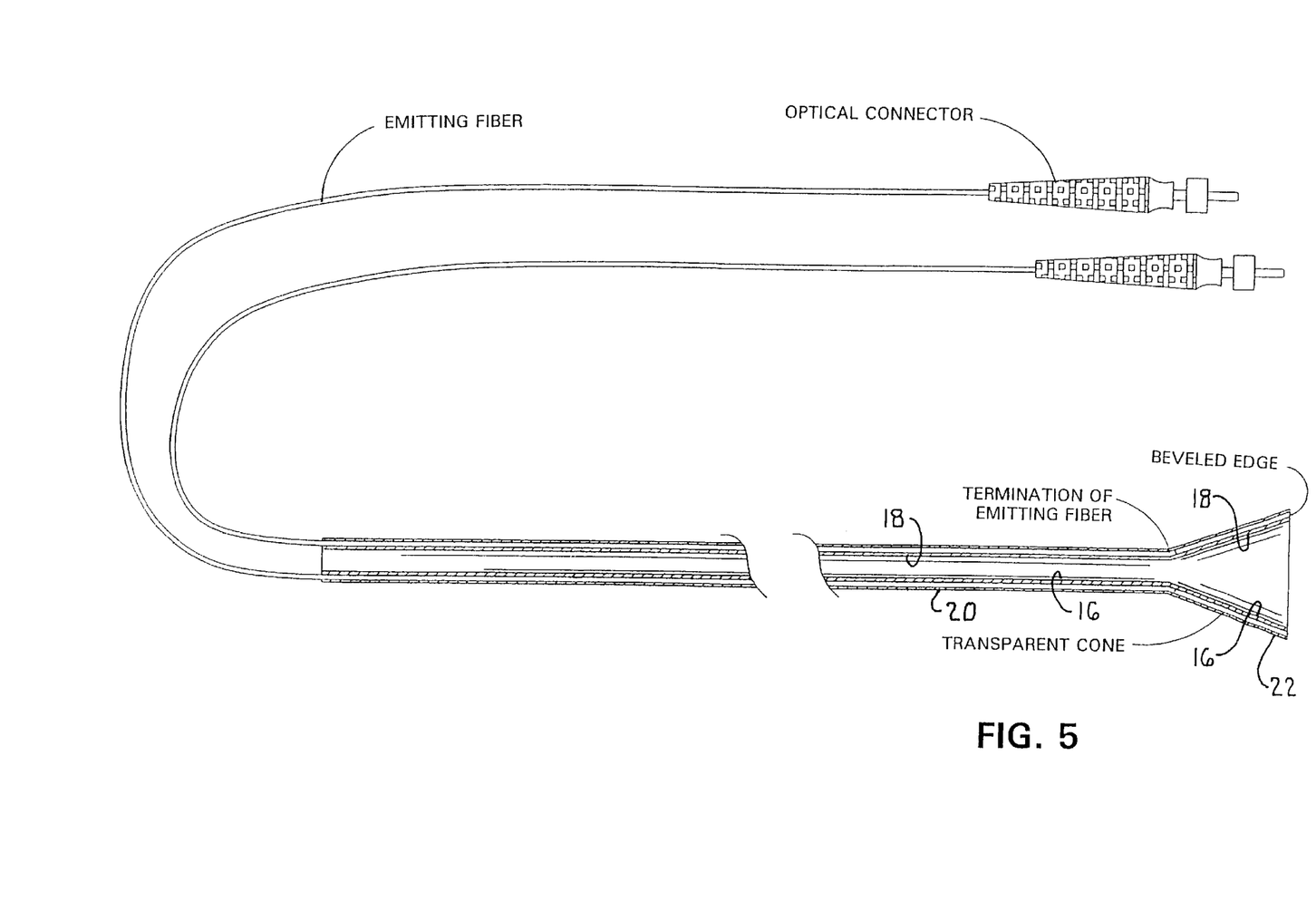
FIG. 5 is a longitudinal view of the CJT using two emitting fibers embedded into the handle and into the wall of a transparent cone.
Figure 6:
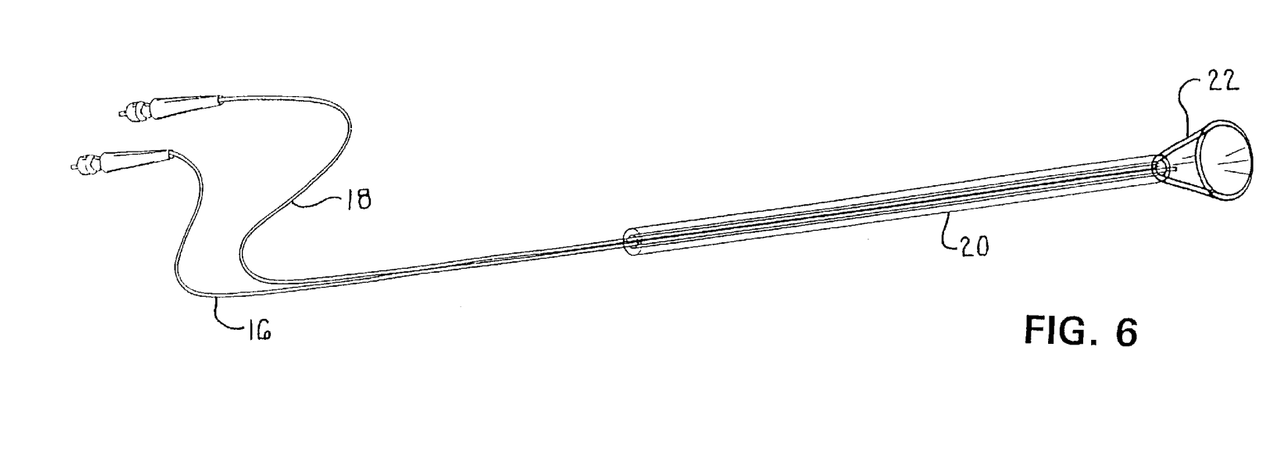
FIG. 6 is an isometric view of the CJT using two emitting fibers embedded into the handle and into the wall of a transparent cone.
Figure 7:
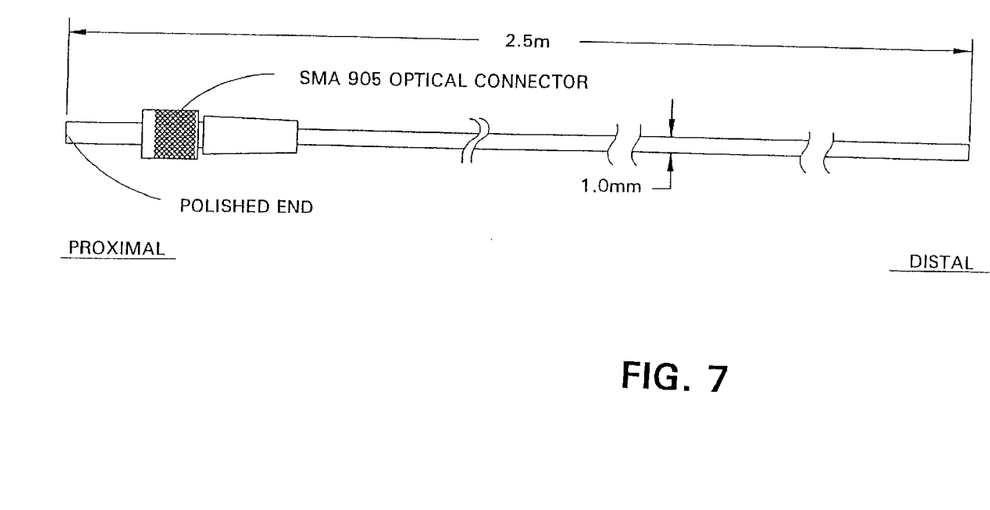
FIG. 7 shows a side of the emitting fiber without the emitting segment used in the fabrication of a transparent CJT.
Figure 8:
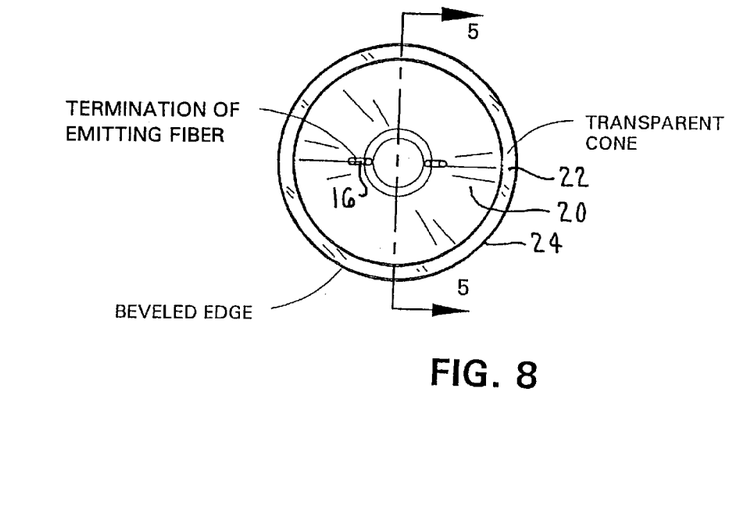
FIG. 8 is an end view of the distal aspect of a transparent cone with the emitting fiber embedded into the wall of a cone.
Figure 9A:
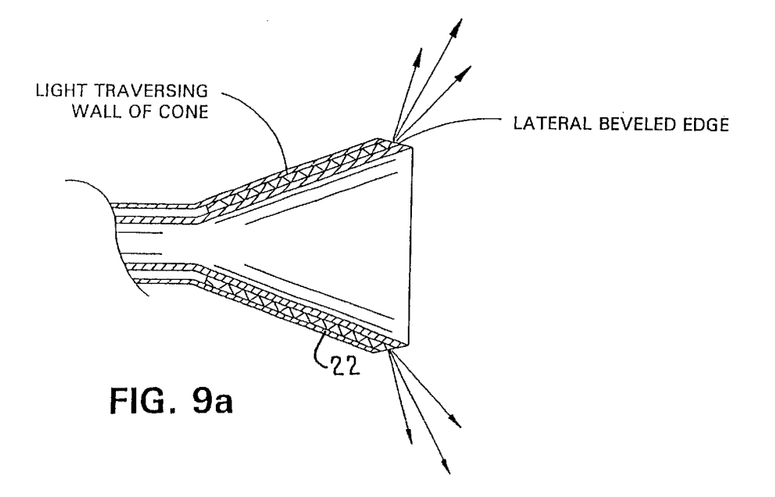
FIGS. 9a, 9b and 9c are longitudinal views of the trans-parent cone showing the lateral, forward, and inward bevels resulting in light that is directed laterally, forwardly, or inwardly from the beveled edge of the transparent cone.
Figure 9B:
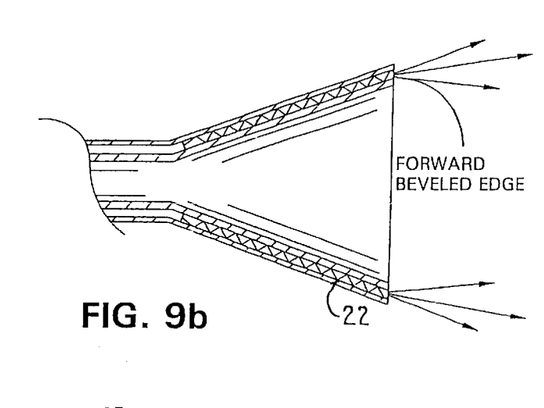
Figure 9C:
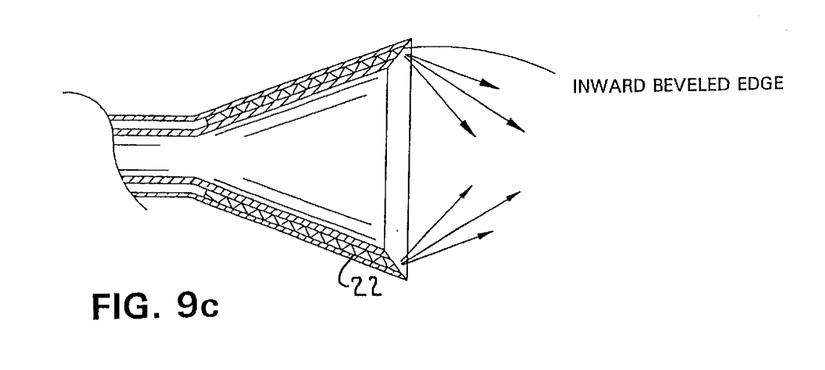

Referring now to FIGS. 5, 6, 7 and 8 of the drawings, the CJT in accordance with the invention is fabricated from a clear transparent polymer such as polymethylmethacrylate or an acrylic with two emitting fibers 16 and 18 embedded in wall 20 of a cone 22. The emitting fiber 16 shown in FIGS. 5, 6 and 7 is depicted in FIG. 8 and has a flat polished end without the scored or abraded emitting segment. The end of the emitting fiber is embedded in the wall 20 of the cone such that light is directed parallel to the outer surface of the cone. The edge 24 of the cone can be beveled to direct light exiting the edge either laterally (FIG. 9a), forward (FIG. 9b), and/or inward (FIG. 9b). The beveled edge 24 of the cone 20 also serves as a template or guide for the surgeon to make an incision along the light line, using the bevel as an incisional platen.

Figure 10A:
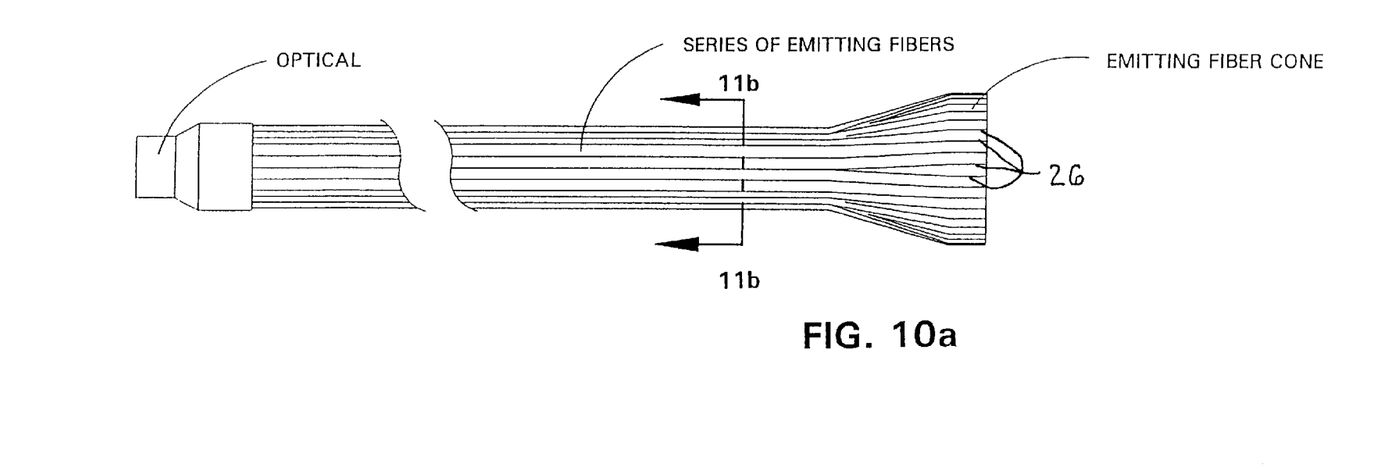
FIGS. 10a, 10b and 10c show a side and cross sectional views of a CJT constructed from a bundle of emitting fibers.
Figure 10B:
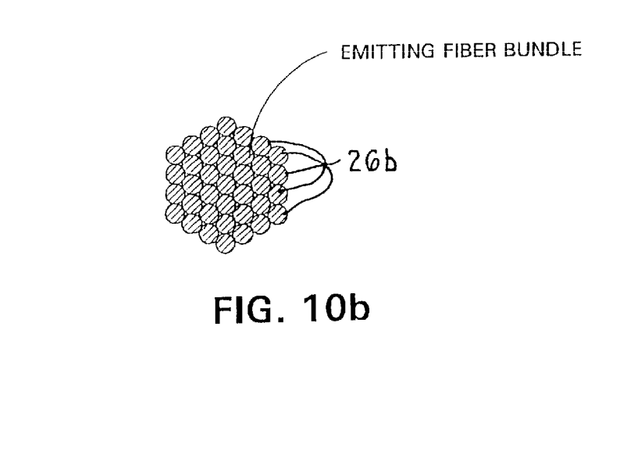
Figure 10C:
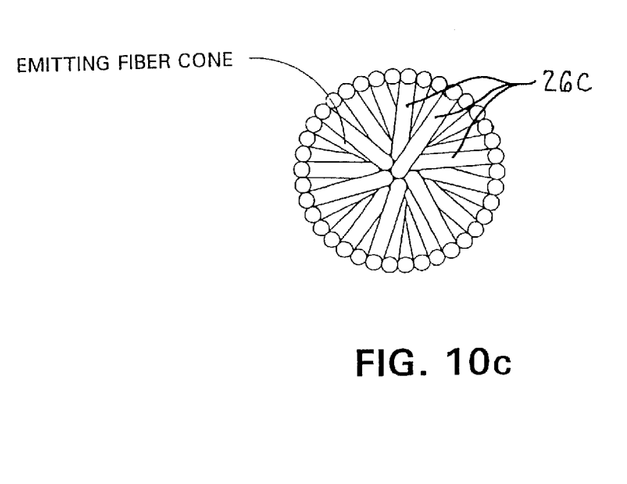

The efficiency of the invention can be improved significantly by increasing the number of emitting fibers embedded in the wall of the cone and/or having the end of the emitting fibers positioned closer to the edge. FIGS. 10a, 10b, and 10c are drawings showing a CJT constructed of many emitting fibers designated by the reference numerals 26a, 26b, and 26c respectively.

Figure 11:
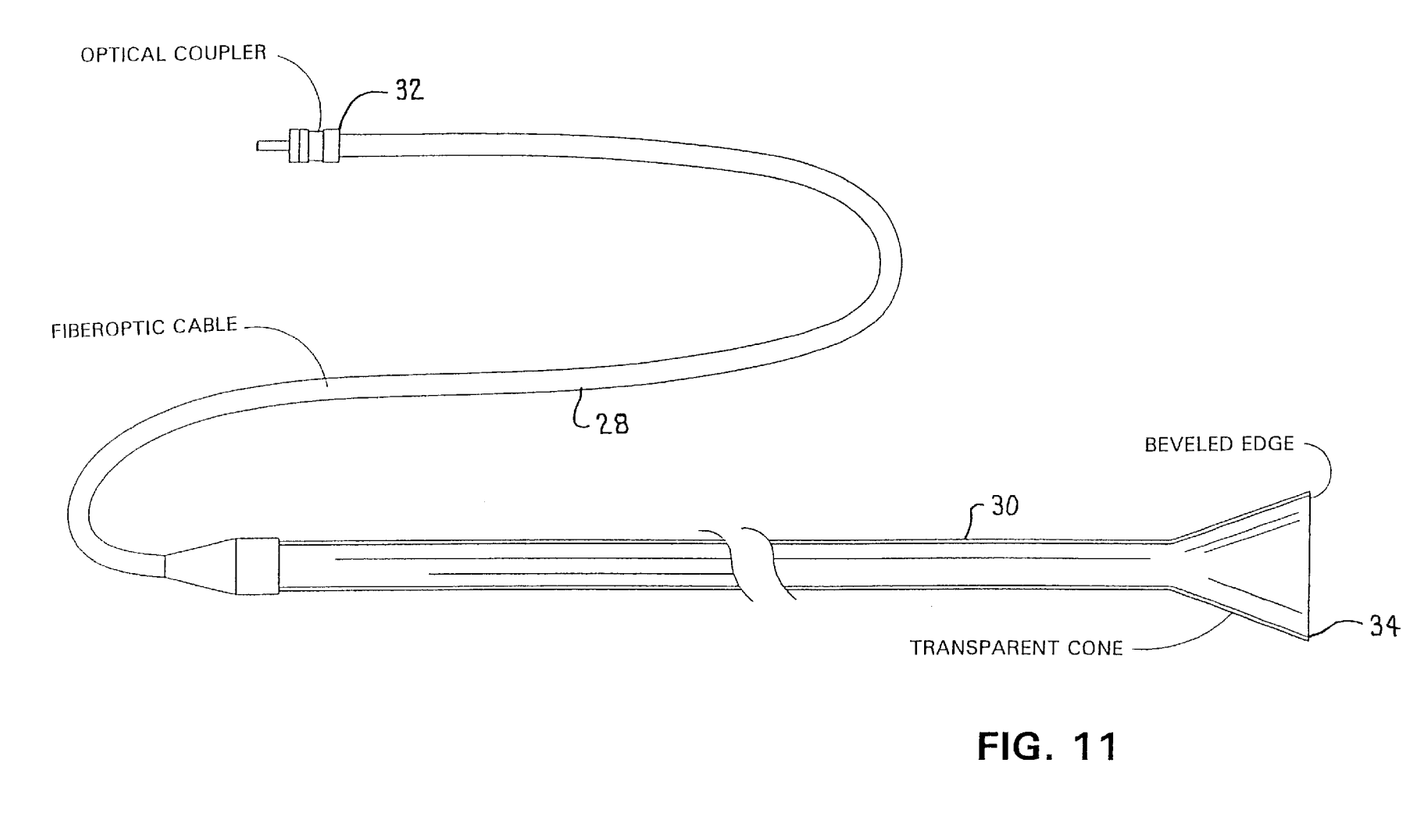
FIG. 11 shows a side view of a CJT constructed of transparent plastic coupled to a fiberoptic optic light guide for coupling to a light source.

Referring to FIG. 11 there is shown a CJT fabricated from cast polymethymethacrylate or an acrylic that has a fiberoptic bundle 28 attached to the proximal end of a handle 30. Optical connector 32 of the fiberoptic cable can be coupled to a high power light source such as a 300 watt xenon light source. When coupled to the light source, light traverses the entire length of the fiberoptic light cable and CJT and exits at beveled edge 34 of the cone.

Figure 12:
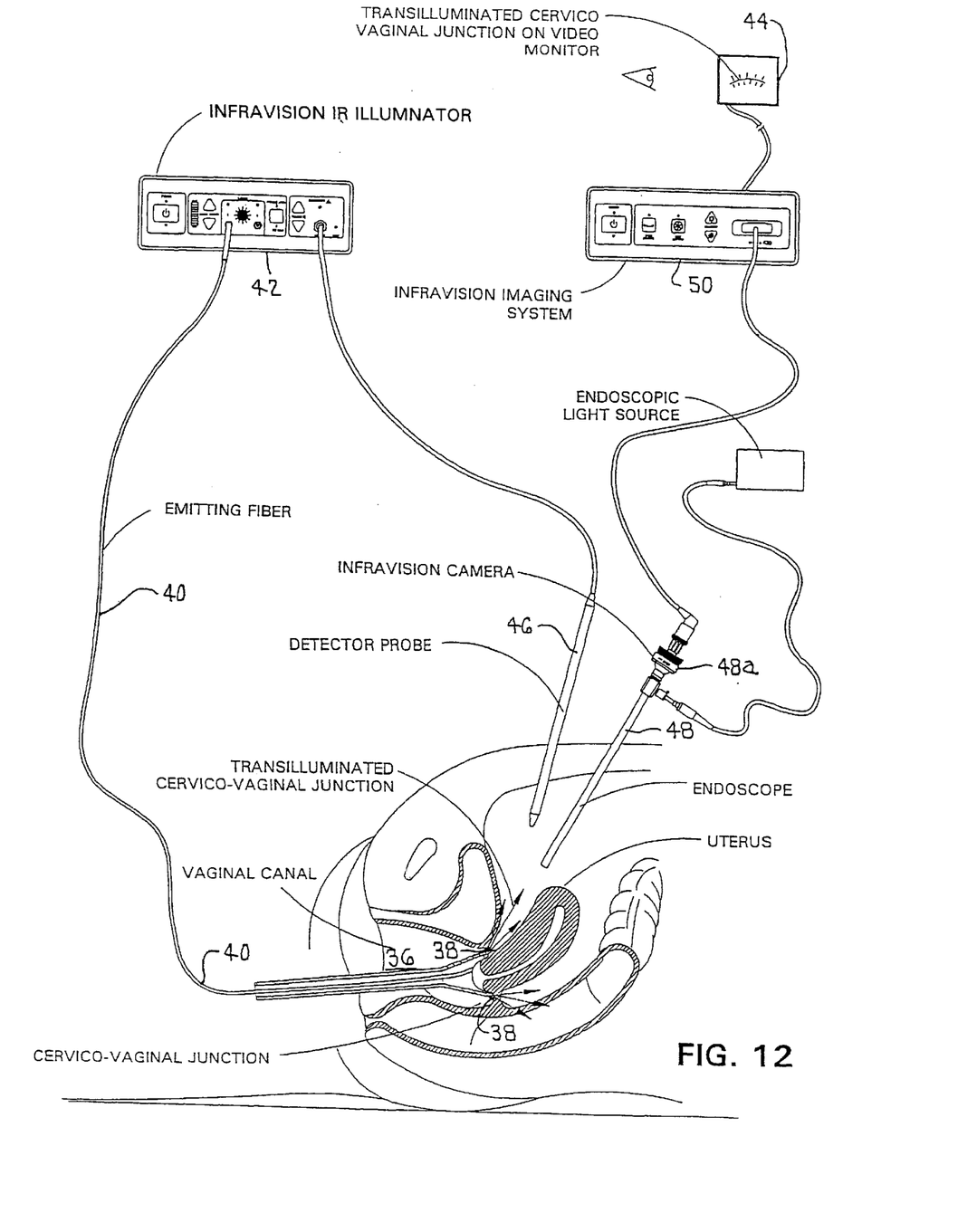
FIG. 12 illustrates the CJT placed at the cervico-vaginal junction and associated with the INFRAVISION IR Illumi-nator along with the INFRAVISION Imaging System during a surgical procedure.

Referring to FIG. 12 of the drawings, the CJT traverses the vaginal canal 36 and is positioned at the cervico-vaginal junction 38. An emitting fiber 40 is connected to the INFRAVISION IR Illuminator 42 as described in the '321 patent. The Illuminator 42 launches light energy into the emitting fiber 40 and transilluminates the cervico-vaginal junction 38. A detector probe 46 may be used to locate the junction 38 by sensing, in this case, the infrared emissions through the junction and providing an audible or visual indication when the probe approaches or is located at the junction. A camera 48a on endoscope 48 may provide light images via an imaging system 50 to the monitor 44, all as set forth in the aforesaid '321 patent and incorporated herein by reference.

Infrared laser diodes of the illuminator 42 can be modulated such that the infrared transilluminated junction appears on video monitor 44 to be "blinking" or the junction appears transilluminated continuously. In this figure, the CJT shown in FIGS. 1, 2, 9 and 10 may be employed as well as others disclosed herein. During laparoscopic procedures either by open abdominal surgery or by instruments inserted into the pelvic region through a trocar, the surgeon is able to detect the junction by either or both of the sensing means and can cut along the junction. The edge of the base of the cone when properly seated provides a guide for the scalpel. During difficult surgical cases when the cervico-vaginal junction is embedded in dense fibrous tissue, the combination of the detection probe and endoscope becomes quite useful. The detector probe can be introduced into the pelvic area through a trocar and visualization of the detector probe on the video monitor allows the surgeon to position and maneuver the detector probe in the approximate area of the infrared transilluminated cervico-vaginal junction. The detector probe is positioned and maneuvered until an audible sound is broadcast from the Light Sensor panel of the INFRAVISION IR Illuminator, which indicates detection of the infrared transilluminated cervico-vaginal junction. During open surgical procedures, the detector probe is introduced into the abdomen and pelvic areas and positioned in the approximate area of the cervico-vaginal junction. The detector probe is maneuvered until an audible sound is broadcast from the INFRAVISION IR Illuminator, which indicates detection of the infrared transilluminated cervico-vaginal junction, thus permitting precise locating of the junction.

Figure 13:
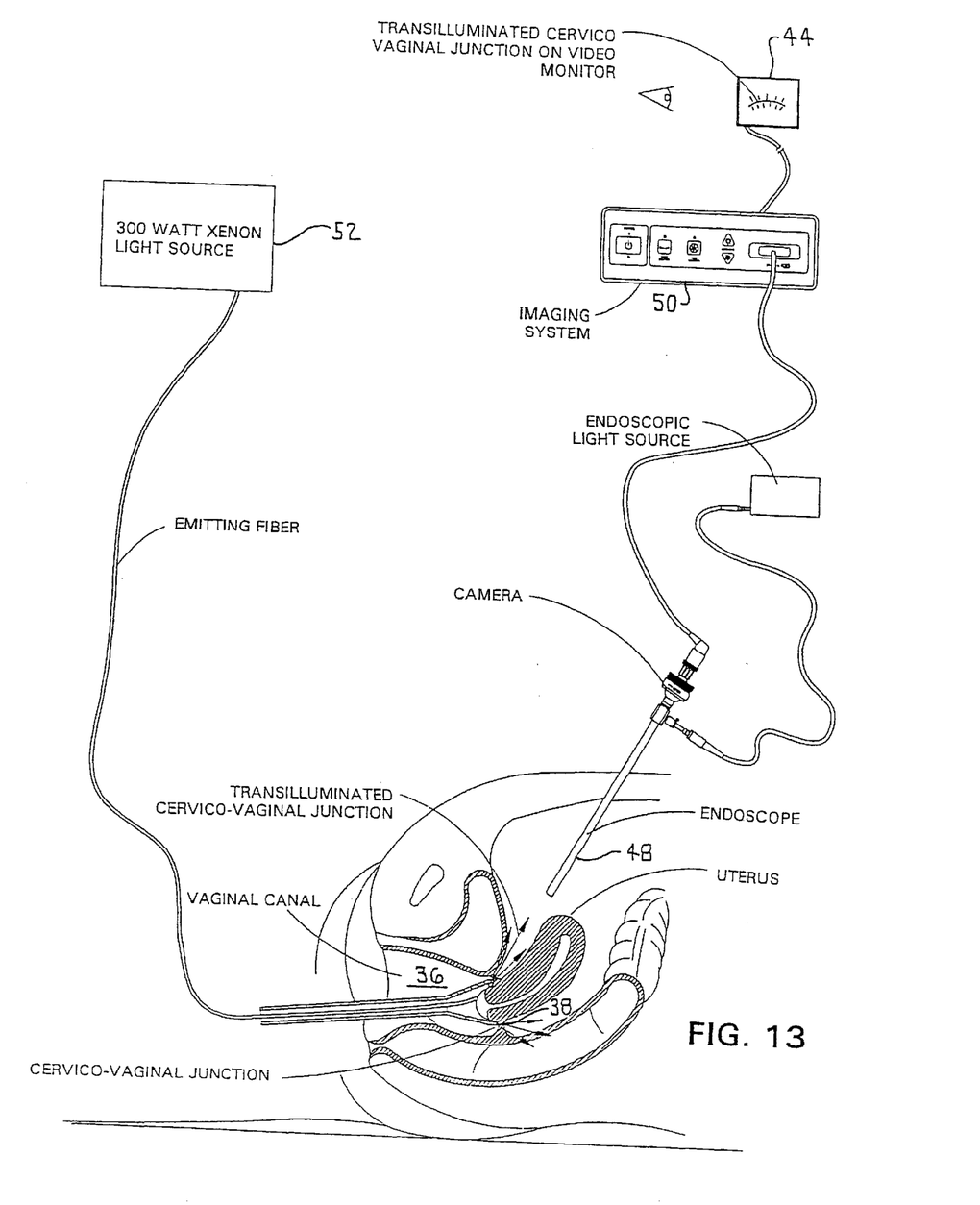
FIG. 13 illustrates the CJT connected to a visible light source and placed at the cervico-vaginal junction while using a typical endoscopic camera for detection of the transilluminated junction during a surgical procedure.

In FIG. 13, the INFRAVISION IR Illuminator has been replaced with a 300 watt xenon light source 52. During endoscopic or open surgical procedures, the transilluminate cervico-vaginal junction 38 can be viewed on a video monitor 44 by using an endoscopic camera 48a or can be seen with direct un-aided vision of the eye.

Figure 14:
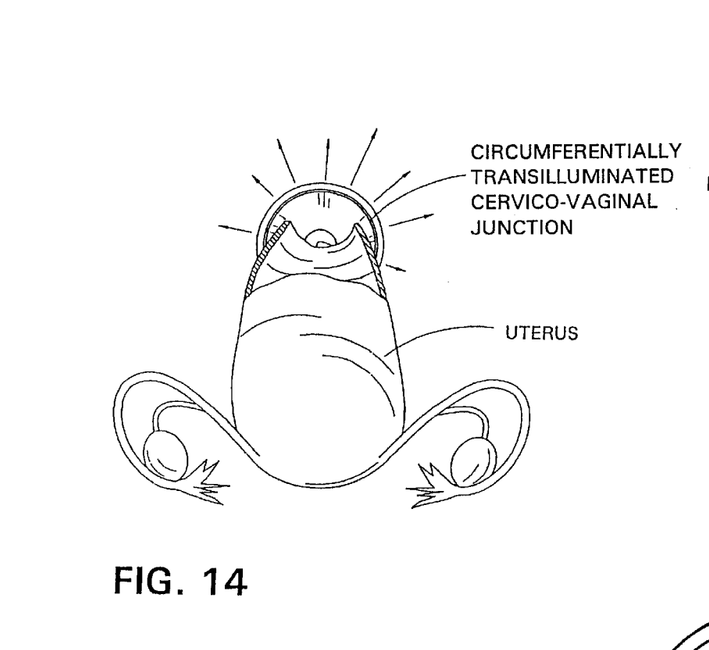
FIG. 14 is an intra-pelvic view of the transilluminated cervico-vaginal junction as seen on the video monitor using the INFRAVISION Imaging System.

Referring to FIG. 14, there is illustrated an intrapelvic view of the transilluminated cervico-vaginal junction using the present invention. Uterus 56 has been severed in this Figure and the base of the cone is visible.

Once given the above disclosure, many other features, modifications and improvements will become apparent to the skilled artisan. Such features, modifications and improvements are, therefore, considered to be a part of this invention, the scope of which is to be determined by the following claims.

What is claimed is:

1. An instrument for illuminating an anatomic junction comprising,
    a cylindrical member having a central axis terminating at its distal end in a curvilinear outwardly flared region defining an arcuate end,
    a light emitting fiber extending through said hollow cylindrical member and having a distal end region that emits light transverse to the length of the fiber,
    said distal end of said fiber secured about said arcuate end of said member,
    at least one detector on the other side of the junction for detecting the light passing through the junction,
    wherein the junction to be illuminated is the cervico-vaginal junction,
    said instrument is adapted to contact said junction from the vaginal side of the junction, and
    said detector is adapted to be located in the pelvic region on the opposite side of the junction.

2. An instrument for illuminating an anatomical junction according to claim 1 wherein,
    said fiber is an infrared emitting fiber.

3. An instrument for illuminating an anatomical junction according to claim 1 wherein
    said light source is an infrared source of light and
    said detector is a detector of infrared energy.

4. An instrument according to claim 1 wherein said arcuate end and the distal end region of said fiber are flared outwardly from said axis.

5. An instrument according to claim 1 wherein
    said arcuate end and the distal end region of said fiber are tapered inwardly relative to said axis.

6. An instrument according to claim 1 wherein
    said outwardly flared region is conical.

7. An instrument according to claim 1 wherein
    said outwardly flared region has the shape of said junction.

8. A system for illuminating an anatomical junction comprising:
    a light source;
    a light emitting fiber having a proximal end connected to said light source and a distal end segment;

a cylindrical probe formed of an optically opaque material having a central axis and an outwardly flared distal end which terminates in a planar surface that defines a distal end opening;

said light emitting fiber extending through said cylindrical probe;

a continuous ring formed of optically transmissive material attached to the distal end of said probe; and wherein the distal end of said light emitting fiber is attached to said ring to transmit light from said light source to said ring.

9. The system according to claim 8 wherein the distal end of said light emitting fiber extends circumferentially around the distal end of said probe to function as said ring.

10. The system according to claim 8 wherein said distal end of said probe is adapted to contact a first side of the anatomical junction; and said system includes a detector adapted to be located on an opposite side of the anatomical junction and configured to detect light emitted by said probe through said anatomical junction.

11. The system according to claim 10 wherein the anatomical junction to be illuminated is the cervico-vaginal junction;

said distal end of said probe is adapted to contact a vaginal side of the cervico-vaginal junction; and said detector is adapted to be located on an opposite side of the cervico-vaginal junction in which said probe is positioned.

12. The system according to claim 8 wherein said outwardly flared distal end is conical.

13. The system according to claim 8 wherein said outwardly flared distal end is shaped complementary to a shape of the anatomical junction.

14. The system according to claim 8 wherein said distal end segment of said light emitting fiber is scored.

15. The system according to claim 8 wherein said light source is a source of infrared light; and said system includes a detector configured to detect infrared light.

16. A system for illuminating an anatomical junction comprising:

a light source;

at least one light emitting fiber having a proximal end connected to said light source and a distal end;

a cylindrical probe having a central axis and an outwardly flared distal end, said distal end having a first circumferentially extending wall that defines a distal end opening wherein said at least one fiber extends through said probe and is disposed against the first circumferentially extending wall that defines the distal end opening and said at least one fiber is formed with a surface adjacent the distal end opening through which light is emitted;

at least one of said first circumferentially extending wall and said distal end of said at least one light emitting fiber being tapered.

17. The system according to claim 16 wherein said distal end of said probe has a second circumferentially extending wall; and said at least one fiber is positioned between said first and second circumferentially extending walls.

18. The system according to claim 17 wherein distal ends of said first and second circumferentially extending walls are co-planar with said distal end of said at least one fiber.

19. The system according to claim 16 wherein a distal end of said first circumferentially extending wall and said distal end of said at least one light emitting fiber are tapered inward with respect to said central axis.

20. The system according to claim 16 wherein a distal end of said first circumferentially extending wall and said distal end of said at least one light emitting fiber are tapered outward with respect to said central axis.

21. The system according to claim 16 wherein said distal end of said probe is adapted to contact a first side of the anatomical junction; and said system includes a detector adapted to be located on an opposite side of the anatomical junction in which said probe is positioned and is configured to detect light transmitted by said probe through the anatomical junction.

22. The system according to claim 21 wherein the anatomical junction to be illuminated is the cervico-vaginal junction;

said distal end of said probe is adapted to contact a vaginal side of the cervico-vaginal junction; and said detector is adapted to be located in a pelvic area on an opposite side of the cervico-vaginal junction in which said probe is positioned.

* * * * *

UNITED STATES PATENT AND TRADEMARK OFFICE
CERTIFICATE OF CORRECTION

PATENT NO. : 6,516,216 B1
DATED : February 4, 2003
INVENTOR(S) : Mark G. Fontenot et al.

It is certified that error appears in the above-identified patent and that said Letters Patent is hereby corrected as shown below:

Column 6,
Lines 26-43, Claim 1, should read:
    1. A system for illuminating a cervico-vaginal junction, said system comprising:
    an illuminator including a cylindrical member having a central axis and being dimensioned to be inserted through the vagina, said cylindrical member having a distal end with an outwardly flared profile and a distal end opening, the distal end being shaped so that the distal end opening fits over the cervix;
    a light emitting fiber extending through said cylindrical member and having a distal end region that emits light transverse to the length of the fiber, said distal end region of said fiber being disposed in said distal end of said cylindrical member; and
    at least one detector adapted to be located in a pelvic region opposite the side of the cervico-vaginal junction in which said illuminator is positioned and being configured to detect light emitted by said illuminator and transmitted through the junction.

Lines 44-46, Claim 2, should read:
    2. The system according to Claim 1 wherein said fiber is an infrared emitting fiber.

Lines 47-51, Claim 3, should read:
    3. The system according to Claim 1 including an infrared light source wherein said at least one detector is a detector of infrared energy.

Lines 52-54, Claim 4, should read:
    4. The system according to Claim 1 wherein said distal end of said cylindrical member and said distal end region of said fiber are tapered outwardly from said axis.

Lines 55-57, Claim 5, should read:
    5. The system according to Claim 1 wherein said distal end of said cylindrical member and said distal end region of said fiber are tapered inwardly relative to said axis.

Lines 58-59, Claim 6, should read:
    6. The system according to Claim 1 wherein said outwardly flared profile is conical.

UNITED STATES PATENT AND TRADEMARK OFFICE
CERTIFICATE OF CORRECTION

PATENT NO. : 6,516,216 B1
DATED : February 4, 2003
INVENTOR(S) : Mark G. Fontenot et al.

It is certified that error appears in the above-identified patent and that said Letters Patent is hereby corrected as shown below:

Column 6 (cont'd),
Lines 60-62, Claim 7, should read:
    7. The system according to Claim 1 wherein said outwardly flared profile has the shape of junction.

Signed and Sealed this

Thirtieth Day of March, 2004

JON W. DUDAS
*Acting Director of the United States Patent and Trademark Office*